United States Patent [19]

Kurobe et al.

[11] Patent Number: 4,853,211

[45] Date of Patent: Aug. 1, 1989

[54] STABLE, EFFERVESCENT VAGINAL SUPPOSITORIES

[75] Inventors: Toshio Kurobe; Masayoshi Kasai; Masanori Kayano, all of Saitama, Japan

[73] Assignee: Eisai Co., Ltd., Tokyo, Japan

[21] Appl. No.: 117,398

[22] Filed: Oct. 28, 1987

Related U.S. Application Data

[63] Continuation of Ser. No. 827,216, Feb. 5, 1986, abandoned, which is a continuation of Ser. No. 628,977, Jul. 12, 1984, abandoned, which is a continuation of Ser. No. 471,453, Mar. 2, 1983, abandoned.

[30] Foreign Application Priority Data

Mar. 5, 1982 [JP] Japan ................................. 57-34034

[51] Int. Cl.$^4$ ............................................. A61K 31/74
[52] U.S. Cl. ........................................ 424/44; 424/78; 514/718; 514/967
[58] Field of Search ..................... 424/44, DIG. 15; 514/892, 966, 967, 78

[56] References Cited

U.S. PATENT DOCUMENTS

| | | | |
|---|---|---|---|
| 3,062,715 | 11/1962 | Reese | 424/44 |
| 4,187,286 | 2/1980 | Marcus | 424/44 |
| 4,288,438 | 9/1981 | Kubo et al. | 514/258 |
| 4,322,399 | 3/1982 | Ahmad et al. | 424/44 |
| 4,323,548 | 4/1982 | Scherm | 424/44 |

OTHER PUBLICATIONS

Gregory, *Use & Applications*, p. 558, (1939).
*Remington's Pham. Sciences*, 16th Ed., p. 1555, (1980).
*Remington's Pharm. Sciences*, pp. 384–385, (1975).
*Physician's Desk Reference* (PDR), p. 1636, (1976).
Handbook of Nonprescription Drugs, 6th Ed., p. 50, (1979).

*Primary Examiner*—Leonard Schenkman
*Attorney, Agent, or Firm*—Wenderoth, Lind & Ponack

[57] ABSTRACT

An effervescent vaginal suppository composition containing a stabilizer appropriately selected from the group consisting of anhydrous sodium sulfate, anhydrous silica gel, dried magnesium silicate, dried aluminum silicate, dried calcium carboxymethylcellulose, dried microcrystalline cellulose, dried starch and dried calcium phosphate or mixtures thereof, preferably in an amount of 0.1–20% based on the weight of said effervescent vaginal suppository composition. Shaped effervescent vaginal suppositories are produced therefrom.

3 Claims, 1 Drawing Sheet

STABLE, EFFERVESCENT VAGINAL SUPPOSITORIES

This application is a continuation of now abandoned application Ser. No. 827,216, filed Feb. 5, 1986 which application is a continuation of now abandoned application Ser. No. 628,977, filed July 12, 1984, which application is, in turn, a continuation of now abandoned application Ser. No. 471,453, filed Mar. 2, 1983.

FIELD OF THE INVENTION

This invention relates to stable, effervescent vaginal suppository compositions and to the suppositories produced therefrom.

DESCRIPTION OF THE PRIOR ART

Effervescent vaginal suppositories have been previously disclosed to the public by Japanese Patent Publication No. 65814/1981 and Japanese Patent Application Laid-open No. 94415/1977. Such vaginal suppositories are those which incorporate a so-called effervescing agent and which generate a gas upon contact with the body fluid upon administration thereby exhibiting an effervescent phenomenon. Effervescing is required in the vagina mainly in such cases where a contraceptive effect is contemplated. Accordingly, this is a technique frequently employed in vaginal suppositories incorporating, for example, a spermatocide. There is also such a case where the effervescing properties are imparted for the purpose of enhancing the rapid disintegration properties of the vaginal suppository itself, but since making the suppository effervescent remarkably impairs the stability of the preparation, this is usually utilized where a contraceptive effect is contemplated. It is widely known that the effectiveness of such suppositories is great.

However, said preparation suffers from poor stability, and has the disadvantage that the neutralization reaction proceeds with time and hence the amount of effervescence is reduced at the time of administration or the packaged product becomes swollen due to the generated gas.

Under such circumstances, the present inventors have studied vaginal suppositories in an effort to eliminate the aforesaid disadvantage and stably maintain the effervescent properties. As a result, they have discovered that the above object may be achieved by incorporating into the suppository formulation the stabilizers described herein.

SUMMARY OF THE INVENTION

Accordingly, the object of this invention is to provide a composition for a vaginal suppository the effervescent properties of which remain stable over an extended period of time. In other words, this invention provides an effervescent vaginal suppository composition which contains one or more stabilizers selected from the group consisting of anhydrous sodium sulfate, anhydrous silica gel, dried magnesium silicate, dried aluminum silicate, dried calcium carboxymethylcellulose, dried microcrystalline cellulose, dried starch and dried calcium phosphate and mixtures thereof.

DETAILED DESCRIPTION OF THE INVENTION

Figure 1:
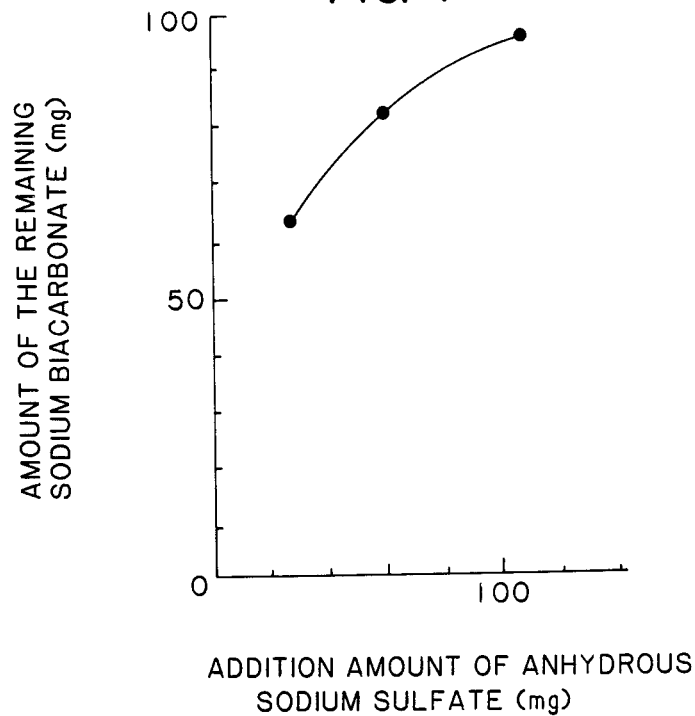
FIG. 1 is a figure showing results obtained in Effect Example 1.

The base for the vaginal suppositories of this inve tion is not particularly restricted, but this is desirab water soluble in order that the neutralization reactic can rapidly proceed upon contact with the body flui Such bases are known in the art.

Therefore, for example, the use of polyethylene gl col as the base presents a preferred embodiment in th invention. Specific examples include mixtures of pol ethylene glycols having molecular weights 1,300–1,600, 950–1,050, 570–630 and 380–420 at appr priate ratios, for example, that containing 70–100% polyethylene glycol having a molecular weight 950–1,050 and 0–30% of polyethylene glycol having molecular weight of 1,300–1,600 or that containii 20–40% of polyethylene glycol having a molecul. weight of 1,300–1,600 and 60–80% of polyethyler glycol having a molecular weight of 570–630.

The effervescing agents employed are likewi: known in the art.

There is no particular restriction on the effervescii agent which imparts the effervescent properties to tl suppositories as long as it is a combination in which : inorganic acid, an organic acid or a water soluble alk; metal salt thereof is employed as an acidic substance ar sodium bicarbonate or potassium bicarbonate is en ployed as a basic substance. It is preferred to emplc phosphoric acid as the inorganic acid, or citric acit tartaric acid, fumaric acid or malic acid as the organ: acid. By the water soluble acid alkali metal salt is meai an acid alkali metal salt which is obtained by partiall neutralizing a polybasic inorganic acid or a polybasi organic acid and which also is water soluble. Exampl thereof include sodium dihydrogenphosphate, sodiui dihydrogencitrate, and the like.

The stabilizer according to this invention, as illu trated in the Effect Examples and Examples describe hereinbelow, may be appropriate selected from tl group consisting of anhydrous sodium sulfate, anh: drous silica gel, dried magnesium silicate, dried alum num silicate, dried calcium carboxymethylcellulos dried microcrystalline cellulose, dried starch and drie calcium phosphate. The use of mixtures of two or moi thereof is also envisaged in this invention.

While there is no particular restriction on the contei of the stabilizer, a preferred range is 0.1–20% based c the weight of the vaginal suppository. Since the suppo itory itself becomes fragile if the content exceeds 20% it is preferred that the content not exceed this uppe limit.

As additional components in the vaginal supposit( ries, it is possible to add effervescing aids, such as an photeric surfactants or ionic or nonionic surfactants, c egg white, gelatin and the like for maintaining the effe: vescence. As will be apparent, these are optional and d not restrict this invention.

The production of the suppositories of this inventic may be practiced in conventional manner for producin said preparations, and, for example, it may be coi ducted as follows:

Firstly, a base, e.g., polyethylene glycol, is melted b heating. A stabilizer according to this invention added, and the mixture is stirred to disperse the stab lizer therein. This mixture is then cooled to a temper:

ture which is 10°-15° C. higher than its solidifying temperature and an effervescing agent is added to form a uniform dispersion. Further, an active agent, for example, a spermatocide, is added and the mixture is stirred to uniformly disperse or dissolve the agent therein. Then this mixture is injected into a mold cavity of a predetermined size and shape and cooled to form a suppository.

Since the suppositories of this invention are, as described above, often utilized in cases where a contraceptive effect is contemplated, it is a preferred embodiment to incorporate a spermatocide as an active agent. As the spermatocide, p-menthanylphenyl polyoxyethylene ether known under the trade name Menfegol is often employed. However, an antibacterial agent, such as tetracycline, an antiinflammatory agent, such as hydrocortisone acetate, or an antifungal agent such as chlordantoin, may be employed.

The effect of this invention is demonstrated by the Effect Examples described hereinbelow.

EFFECT EXAMPLE 1

Samples and Procedures

To a mixture of 60 mg of Menfegol, 5 mg of dioctyl sodium sulfosuccinate, 200 mg of potassium hydrogentartrate, 100 mg of sodium bicarbonate and 1,105 mg, 1,075 mg and 1,035 mg of a base comprising polyethylene glycols having molecular weights of 950–1,050 and 1,300–1,600 was added 30 mg, 60 mg or 100 mg of anhydrous sodium sulfate to prepare three different suppositories having a total weight of 1.5 g respectively. These were used as samples and stored at 37° C. for a month. The amount of the remaining sodium bicarbonate after storage was determined.

Results

The results are given in FIG. 1. From FIG. 1, it can be seen that anhydrous sodium sulfate exerts the stabilizing effect of this invention.

EFFECT EXAMPLE 2

Samples and Procedures

Four different vaginal suppositories were prepared by procedures similar to those described in Effect Example 1 except that the anhydrous sodium sulfate was employed in amounts of 10 mg, 50 mg, 100 mg and 200 mg respectively. These were used as samples and stored at 37° C. for a month, and the effervescing properties after storage were determined. The effervescing properties were determined by adding 3 ml of water at 37° C. and periodically measuring the effervescence volume.

Results

Figure 2:
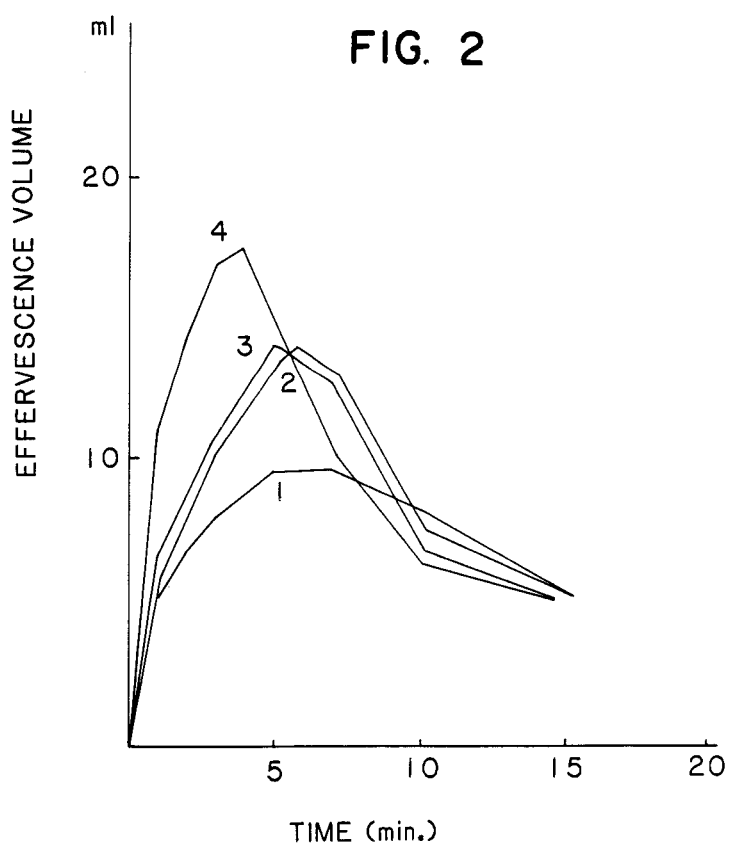
FIG. 2 is a figure showing results obtained in Effe Example 2.

The results are given in FIG. 2. In FIG. 2, the curves depicted by the numerals 1, 2, 3 and 4 indicate the change in the effervescence volume with the time where the anhydrous sodium sulfate is added in amounts of 10 mg, 50 mg, 100 mg and 200 mg respectively. It can be seen from FIG. 2 that anhydrous sodium sulfate exerts the stabilizing effect of this invention.

EFFECT EXAMPLE 3

Samples and Procedures

Effervescent vaginal suppositories which were prepared by procedures similar to those described in Example 1 except that the anhydrous sodium sulfate was replaced by the stabilizers as set forth in the column of the stabilizer in Table 1 were used as samples and stored at 37° C. for a month. Thereafter, the change in the appearance (swelling of the package) and the maximum effervescence volume were examined.

Results

The results are given in Table 1.

TABLE 1

| Stabilizer | Change in Appearance after Storing at 37° C. for a Month | Maximum Effervescence Volume | |
|---|---|---|---|
| | | Immediately after Production | After a Month at 37° C. |
| Not added | Swollen | 18.0 ml | 13.50 ml |
| Dried magnesium silicate | No change | 20.0 ml | 21.85 ml |
| Dried aluminum silicate | No change | 19.4 ml | 20.2 ml |
| Dried calcium carboxymethylcellulose | No change | 17.6 ml | 17.4 ml |
| Dried microcrystalline cellulose | No change | 23.7 ml | 23.0 ml |
| Dried calcium monohydrogenphosphate | No change | 24.9 ml | 22.0 ml |

From Table 1, it can be seen that the effect of this invention is imparted by the stabilizers set forth in Table 1.

EFFECT EXAMPLE 4

Samples and Procedures

The effervescent vaginal suppository described in Example 3 (specimen) and a suppository obtained by excluding the anhydrous silica gel from said suppository (control) and the effervescent vaginal suppository described in Example 4 (specimen) and a suppository obtained by excluding the dried corn starch from said suppository (control) were used as samples and stored at 37° C. for a month. Thereafter, the change in the appearance (swelling) of the package) and the maximum effervescence volume were examined.

Results

The results are given in Table 2.

TABLE 2

| Sample | Change in Appearance after Storing at 37° C. for 1 month | Maximum Effervescence Volume | |
|---|---|---|---|
| | | Immediately after Production | After 1 month at 37° C. |
| Example 3 | | | |
| Control | Swollen | 24.5 ml | 14.4 ml |
| Specimen | No Change | 20.5 ml | 19.0 ml |
| Example 4 | | | |
| Control | Swollen | 20.0 ml | 13.5 ml |
| Specimen | No change | 12.0 ml | 12.8 ml |

From Table 2, it can be seen that the effect of this invention is imparted by anhydrous silica gel and dried corn starch.

This invention is more particularly described by the following Examples.

EXAMPLE 1

80.0 g of polyethylene glycol (average molecular weight 950–1,050), 23.5 g of polyethylene glycol (average molecular weight 1,300–1,600), 6.0 g of Menfegol and 0.5 g of dioctyl sodium sulfosuccinate were melted together by heating to obtain a uniform mixture. To this mixture was added 5.0 g of anhydrous sodium sulfate and the mixture was stirred thoroughly to disperse. Then, 10.0 g of sodium bicarbonate, 25 g of potassium hydrogentartrate and 0.15 g of saponin were added successively, stirred and kneaded to uniformly disperse. The mixture was injected, while hot, into a mold having a predetermined shape and cooled to below room temperature. Thereby, an effervescent vaginal suppository having a spermatocidal effect and weighing 1.5 g per unit was obtained.

EXAMPLE 2

A spermatocidal effervescent vaginal suppository (3.0 g/unit) having the following composition was prepared by procedures similar to those described in Example 1.

| | |
|---|---|
| Polyethylene glycol (molecular weight 1,300–1,600) | 74.6 g |
| Polyethylene glycol (molecular weight 570–630) | 111.9 g |
| Menfegol | 6.0 g |
| Dioctyl sodium sulfosuccinate | 0.5 g |
| Sodium bicarbonate | 25 g |
| Monosodium fumarate | 50 g |
| Anhydrous sodium sulfate | 20 g |
| Egg white | 12 g |

EXAMPLE 3

An effervescent vaginal suppository (2 g/unit) having the following composition was prepared by procedures similar to those described in Example 1.

| | |
|---|---|
| Polyethylene glycol (molecular weight 950–1,050) | 116.6 g |
| Tetracycline | 0.2 g |
| Dioctyl sodium sulfosuccinate | 0.2 g |
| Sodium bicarbonate | 20.0 g |
| Monopotassium dihydrogenphosphate | 45.0 g |
| Anhydrous silica gel | 10.0 g |
| Methylcellulose | 8.0 g |

EXAMPLE 4

An effervescent vaginal suppository (3.0 g/unit) having the following composition was prepared by procedures similar to those described in Example 1.

| | |
|---|---|
| Polyethylene glycol (molecular weight 1,300–1,600) | 68.8 g |
| Polyethylene glycol (molecular weight 950–1,050) | 275.2 g |
| Hydrocortisone acetate | 1 g |
| Sodium laurylsulfate | 0.2 g |
| Sodium bicarbonate | 20.0 g |
| Monosodium dihydrogencitrate | 50.0 g |
| Dried corn starch | 3.0 g |
| Polyvinylpyrrolidone | 12.0 g |

EXAMPLE 5

An effervescent vaginal suppository (2.5 g/unit) having the following composition was prepared by procedures similar to those described in Example 1.

| | |
|---|---|
| Polyethylene glycol (molecular weight 950–1,050) | 201.5 g |
| Chlordantoin | 3.0 g |
| Dodecylaminoethylglycine (30%) | 2.5 g |
| Potassium bicarbonate | 8.0 g |
| Tartaric acid | 10.0 g |
| Anhydrous sodium sulfate | 25.0 g |

What is claimed is:

1. An effervescent vaginal suppository composition which consists essentially of:
   (A) from about 0.1 to about 20 percent, based upon the weight of the suppository composition, of anhydrous sodium sulfate as stabilizer,
   (B) an amount sufficient to achieve effervescence upon contact with vaginal body fluid of an effervescing agent which is a combination of:
      (1) at least one acidic substance selected from the group consisting of phosphoric acid, citric acid, tartaric acid, fumaric acid, malic acid and water soluble acid alkali metal salts thereof, and
      (2) at least one basic substance selected from the group consisting of sodium bicarbonate and potassium bicarbonate,
   the ratio of (1):(2) being sufficient to achieve effervescence of the composition upon contact with vaginal body fluid,
   (C) a base for vaginal suppository, and
   (D) an effective amount of a member selected from the group consisting of a spermatocide, an antibacterial agent, and antiinflammatory agent and an antifungal agent.

2. An effervescent vaginal suppository composition according to claim 1 wherein the base for the composition is polyethylene glycol.

3. An effervescent vaginal suppository composition according to claim 1 in the form of a suppository.

* * * * *